United States Patent [19]

Davis

[11] Patent Number: 5,332,184

[45] Date of Patent: Jul. 26, 1994

[54] POLE CLAMP ASSEMBLY AND A METHOD OF ITS USE

[75] Inventor: Richard C. Davis, Palm Harbor, Fla.

[73] Assignee: TREK Medical Corporation, Tampa, Fla.

[21] Appl. No.: 18,283

[22] Filed: Feb. 16, 1993

[51] Int. Cl.⁵ .............................................. A47B 96/06
[52] U.S. Cl. .................................. 248/231.4; 24/525; 24/569; 248/230
[58] Field of Search ............... 248/231.4, 231.5, 230, 248/125; 24/525, 522, 569, 514, 490

[56] References Cited

U.S. PATENT DOCUMENTS

| | | | |
|---|---|---|---|
| 1,516,489 | 11/1924 | Barton | 24/525 X |
| 1,609,666 | 12/1926 | Settevig . | |
| 2,682,694 | 7/1954 | Kempkes | 24/569 |
| 3,013,756 | 12/1961 | Boston | 248/113 |
| 3,672,619 | 6/1972 | Bowen | 248/113 |
| 4,190,224 | 2/1980 | Le Blanc et al. | 248/229 |
| 4,593,422 | 6/1986 | Wolpert | 24/525 X |
| 4,600,209 | 7/1986 | Kerr, Jr. | 280/400 |
| 4,674,722 | 6/1987 | Danby | 24/569 X |
| 4,767,131 | 8/1988 | Springer et al. | 280/289 |
| 4,871,278 | 10/1989 | Gerlach | 24/525 X |
| 5,169,106 | 12/1992 | Rasmussen | 248/230 |
| 5,219,428 | 6/1993 | Stern | 248/231.4 |

Primary Examiner—J. Franklin Foss
Attorney, Agent, or Firm—Griffin Butler Whisenhunt & Kurtossy

[57] ABSTRACT

A pole clamp assembly (10), and a method of using same, involves two jaws (14, 16) mounted on a base frame, or housing, (12) with a first (14) of the jaws being movable on the frame along two parallel curved tracks between closed and open positions and a selectively-actuatable biasing mechanism (18) comprising an elastic or spring member (38, 102) attached between the movable jaw (14) and a reel or hub (36, 36'). By selectively moving the hub between open and closed positions, the biasing mechanism moves the jaw between the closed and open positions, but if the jaw is held in the closed position, for example, which it will be if the clamp is engaged with a pole, the biasing mechanism flexes when the hub is moved to the open position to allow the movable jaw to remain in the closed position. When the jaw is no longer held in the closed position it snaps to the open position under the influence of the biasing mechanism. Additionally, a spring loaded lock (100) which holds the movable jaw in the open position can be automatically actuated by placing a member to be clamped between the two jaws to automatically release the movable jaw, thereby allowing it to snap to the closed position under the influence of the biasing mechanism.

18 Claims, 4 Drawing Sheets

POLE CLAMP ASSEMBLY AND A METHOD OF ITS USE

BACKGROUND OF THE INVENTION

This invention relates generally to the art of pole clamp assemblies and more specifically to clamp assemblies which can be mounted on mobile personal supports, such as wheelchairs and hospital beds, for supporting IV-poles as well as to objects which can be attached to vertical poles, such as IV pumps.

A problem encountered in medical facilities, such as hospitals, nursing homes, and the like, when patients are moved is that the patients are often attached, via intravenous (IV) tubes, to pumps and containers which feed fluids to them. These fluids are of a variety of different kinds, including blood, nutrients, medicines, and the like. Such apparatus, e.g. pumps and containers, can be quite heavy for an individual patient, often weighing as much as 50 pounds. In order to support such apparatus, medical facilities usually use IV-poles extending upwardly from wide bases with castors thereon; thus, the IV-poles can be rolled from one place to another, as required. When patients are moved short distances, these mobile IV-poles are normally rolled with them. However, when the patients are put on litters, or in wheelchairs, for example, and moved moderate to great distances, it is inconvenient and dangerous to roll separate IV-poles therewith and this often requires an undue number of personnel to effectively and safely accomplish it. It is therefore an object of this invention to provide a pole clamp assembly with which an IV-pole can be selectively and easily clamped to and unclamped from a mobile patient support so that it can be easily transported with the patient support in a convenient and safe manner by one person.

A related problem is encountered in medical facilities when one attempts to mount a heavy object, such as pumps, containers and the like on IV-poles. That is, it is often difficult for nurses and other medical personnel to hold such items while clamping them to the IV-poles. Thus, it is a further object of this invention to provide a clamping apparatus for attaching such objects to poles.

Clamps for intravenous poles are suggested in U.S. Pat. No. 4,190,224 to LeBlanc et al., U.S. Pat. No. 4,600,209 to Kerr and U.S. Pat. No. 4,767,131 to Springer et al. The IV-pole of LeBlanc et al. is a specialized pole for use with the clamp disclosed therein and the clamp would be difficult and time-consuming to employ. The pole of this patent cannot be easily used by itself in the manner of normal mobile IV-poles and it is difficult to use it separately from a patient support such as a bed or a wheelchair. Further, the clamp disclosed therein does not enable one to transport a conventional mobile IV-pole with a mobile patient support. Therefore, it is an object of this invention to provide an intravenous pole holder which can be easily employed on a mobile patient support to effectively transport a conventional mobile IV-pole with the mobile patient support.

The transport support disclosed in Kerr can be used with separately-supported, mobile, IV-poles, however, it does not appear to be sufficiently secure for many hospital circumstances, employing VELCRO and/or straps to attach a pole to a mobile patient support. It does not appear, for example, that this device can support loaded IV-poles weighing upwards to 50 pounds from the ground; thus, castors of IV-poles would drag along a floor as a mobile patient support is transported, thereby causing drag on the patient support and problems for hospital personnel. For example, if the castors were to get caught on a floor irregularity, the IV-pole might be caused to topple. This could injure the patient directly or by forcibly removing the IV lines from him, cause him injury indirectly when the proper fluids are not fed to him. Thus, it is an object of this invention to provide a pole clamp assembly which is sufficiently strong to securely hold a pole weighing upwards of 50 pounds from the ground.

Although the utility clamp of Springer (U.S. Pat. No. 4,767,131) does operate with a conventional IV-pole, it is for use with a specialized wheelchair. It would be difficult, and possibly dangerous, for an operator to use the clamp described therein to attach a conventional IV-pole to a mobile patient support so that the IV-pole is not touching the floor.

There are many prior art clamps which could be used to clamp IV-poles to mobile patient supports. However, most of them suffer from one or more of the following deficiencies:

They do not hold poles in a sufficiently sturdy manner to ensure that IV-poles weighing upwards to 50 pounds are stable and cannot, under all normal circumstances, fall;

it is difficult and time-consuming to mount heavy IV-poles to them so as to provide the required sturdiness;

personnel cannot mount heavy poles to them while using both hands to lift the poles, as is often desirable in hospital settings;

personnel cannot detach heavy poles from them while using both hands to lift the poles as is also often desirable in hospital settings; and, personnel cannot attach them to, nor detach them from, light poles with one hand, which is often desirable.

Therefore, it is an object of this invention to provide a pole clamp assembly which overcomes these deficiencies.

It is a further object of this invention to provide a pole clamp assembly which is inexpensive and uncomplicated to manufacture but yet effective in operation.

Additionally, in hospital settings, it is often necessary to attach pumps and other devices to vertical poles, such as IV-poles. These devices are usually heavy and bulky and it therefore requires the use of both hands to lift and position them onto the poles so that no hand is free for fastening a clamp. It is, therefore, an additional object of this invention to provide a clamping mechanism which can be preloaded to automatically snap shut when such a device is properly positioned on a vertical pole such as an IV-pole.

SUMMARY OF THE INVENTION

According to principles of this invention, a pole clamp assembly comprises a base frame having two jaws mounted thereon, at least a first of which is movable between closed and open positions, and a selectively-actuatable biasing mechanism which is linked to the movable jaw for being selectively placed in a biasing mode in which it allows the movable jaw to be in one of the closed and/or open positions while urging it toward the other position, or in a non-biasing mode, in which it allows the movable jaw to be in one of the open and closed positions without substantially urging the movable jaw toward the other position.

BRIEF DESCRIPTION OF THE DRAWINGS

The invention is described and explained in more detail below using the embodiments shown in the drawings. The described and drawn features, in other embodiments of the invention, can be used individually or in preferred combinations. The foregoing and other objects, features and advantages of the invention will be apparent from the following more particular description of a preferred embodiment of the invention, as illustrated in the accompanying drawings in which reference characters refer to the same parts throughout the different views. The drawings are not necessarily to scale, emphasis instead being placed upon illustrating principles of the invention in a clear manner.

DESCRIPTION OF TEE PREFERRED EMBODIMENT

Figure 1:
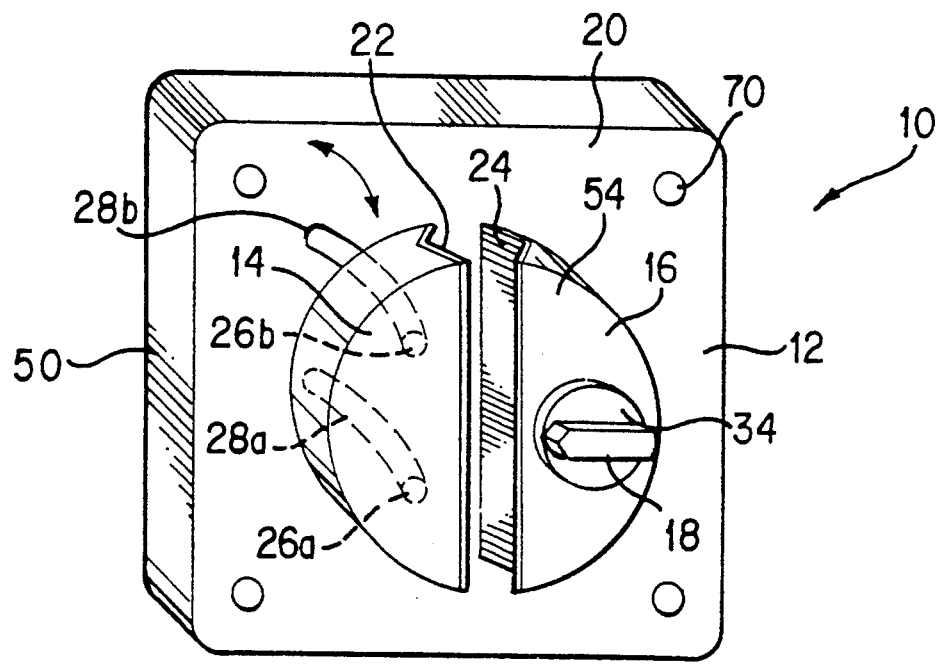
FIG. 1 is a front isometric view of a pole clamp assembly of this invention.

A pole clamp assembly 10 comprises a base frame in the form of a housing 12, first and second jaws 14 and 16 mounted on the housing 12 and a selectively actuatable biasing mechanism 18. The second, or fixed, jaw 16 is affixed to a face plate 20 of the housing 12 while the first, or movable, jaw 14 is movably mounted on the face plate so that a concaved movable-jaw mouth 22 is movable toward and away from a concaved fixed-jaw mouth 24. In this respect, the movable jaw 14 has lower and upper movable-jaw followers 26a and b which ride in jaw-guide tracks formed by lower and upper slots 28a and b in the face plate 20. It should be noted that the curved slots 28a and b angle, arc, or curve, from an attitude almost perpendicular to an interface 30 between the movable and fixed jaws 14 and 16 at an upper end (furthest from the interface) to an attitude almost parallel to the interface at a lower end (closest to the interface). Thus, the movable jaw 14 is moved in an arch, or curve, defined by the arch or curve of the lower and upper slots 28a and b when it is moved between a closed position (in which its lower and upper movable-jaw followers 26a and b are at lower ends of their respective lower and upper slots 28a and b) and an open position (in which the movable jaw followers 26a and b are at upper ends of the slots 28a and b), but maintains the same attitude throughout this movement so that its movable-jaw mouth 22 remains approximately parallel to the fixed-jaw mouth 24. In a preferred embodiment, the movable-jaw mouth 22 and the fixed-jaw mouth 24 have resilient layers 32 (FIG. 2) thereon so that these mouths can more firmly grip a pole 74.

It will be understood by those of ordinary skill in the art that, because of the curved configuration of the lower and upper slots 28a and b, if downward force is applied to the first movable jaw 14 when it is at the top ends of the lower and upper slots 28a and b, as viewed in FIG. 1, then this force is at first translated into relatively great lateral movement of the movable jaw 14 toward the fixed jaw 16, but with a relatively little force. But as the movable-jaw mouth 22 of the movable jaw 14 approaches the fixed-jaw mouth 24 of the fixed jaw 16, this downward force is translated into less movement by the movable-jaw mouth 22 toward the fixed-jaw mouth 24, but into greater force in that direction. In other words, as the pole clamp assembly of FIG. 1 is moved from an open position, in which the movable-jaw followers 26a and b of the first movable jaw 14 are at the upper ends of the lower and upper slots 28a and b, toward a closed position, in which the lower and upper movable-jaw followers 26a and b are at lower ends of the lower and upper slots 28a and b, the mechanical advantage of force increases.

Figure 3:
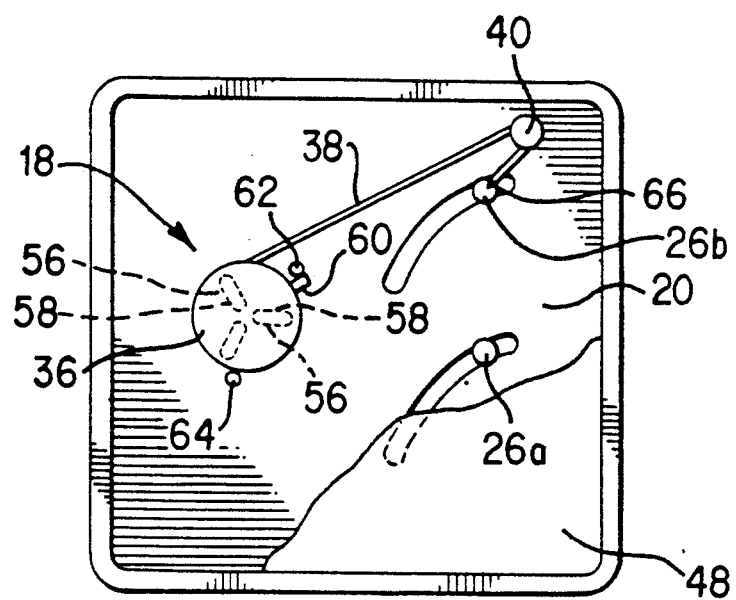
FIG. 3 is a partially cut-away rear-elevational view of the pole clamp assembly of FIG. 1, with a back plate thereof being partially cut away.

The selectively-actuatable biasing mechanism 18 comprises a clamp-adjusting knob 34, a hub 36, an elastic cord 38, a pulley 40, and a knob-position bias spring 42. The clamp-adjusting knob 34 is mounted on a front surface of the second jaw 16, where it is readily accessible, by means of a shaft 44 which extends through a hole in the second jaw 16 into a housing cavity 46 defined by the face plate 20, a removable back plate 48, and a sidewall 50 of the housing 12. In the housing cavity 46, the shaft 44 is affixed to the hub 36 which can be rotated by rotating the clamp-adjusting knob 34. It should be noted that the shaft 44 is sufficiently long so that an inner facing 52 of the clamp-adjusting knob 34 can stand away from an outer facing 54 of the second, or fixed, jaw 16. In this regard, the hub 36 is, in fact, forced against the face plate 20 by means of the knob-position biasing spring 42 which is located between the hub 36 and the back plate 48 so that the clamp-adjusting knob 34 is, in fact, forced away from the outer facing 54 of the fixed jaw 16. In FIG. 3 it can be seen that the hub 36, on a facing thereof directed toward the face plate 20, has protrusions 56 and that the face plate 20 has indentations 58 corresponding to the protrusions. Both the protrusions 56 and the indentations 58 are spaced at intervals of 120° about the hub 36. Further, the hub 36 has a hub stop pin 60 mounted on its periphery and there are an open stop 62 and a closed stop 64 mounted on the face plate 20 which are impinged on by the hub stop pin 60, thereby determining the extent of angular rotation allowable to the hub 36. The open stop 62 and the closed stop 64 can be located approximately 120° from one another.

The elastic cord 38 is attached to and wrapped about the hub 36 in a counterclockwise direction as depicted in FIG. 3 and extends about the pulley 40 with a jaw-attachment end 66 thereof being attached to the upper movable-jaw follower 26b. When the hub stop pin 60 impinges on the open stop 62, a sufficient amount of the elastic cord 38 is wrapped about the hub 36 so that if there is nothing clamped in the pole clamp assembly, the amount of elastic cord 38 extending between the hub 36 and the movable-jaw follower 26b is shortened to thereby move the upper movable-jaw follower 26b and the attached first, movable, jaw 14 to an open position in which its mouth 22 is spaced above and far away from the fixed-jaw mouth 24. However, when the clamp-adjusting knob 34 is rotated so that the hub stop pin 60 impinges on the closed stop 64, the elastic cord 38 between the hub 36 and the upper movable-jaw follower 26b is lengthened, thereby allowing gravity to act downwardly on the first movable jaw 14 so that its movable-jaw mouth 22 moves downwardly and close to the fixed-jaw mouth 24.

Describing now the method of operation of the pole clamp assembly 10 and the method of its use, the pole clamp assembly 10 is attached to a mobile patient support 68 by means of pins or bolts 70 passing through the housing 12 which are attached to a mounting plate 72, thereby clamping the pole clamp assembly 10 to the mobile patient support 68.

Figure 2:
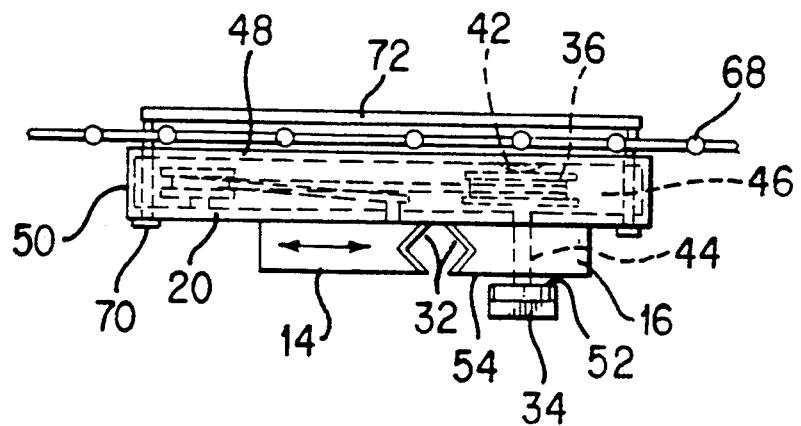
FIG. 2 is a top view of the pole clamp assembly FIG. 1 mounted on a movable support depicted in fragmented fashion therein.

Assuming now that the mobile patient support 68, such as a gurney, does not have a patient thereon and that the pole clamp assembly 10 is not being used to support an IV-pole 74 as is shown in FIGS. 1 and 2, the clamp adjusting knob 34 is in an open position (according to FIG. 3), although it is shown to be in the closed position in FIGS. 1 and 2. The clamp adjusting knob 34 was moved to the open position by depressing it inwardly against the pressure of the bias spring 42 so that its inner facing 52 contacted the outer facing 54 of the fixed jaw 16, in which position the protrusions 56 of the hub 36 disengaged from the indentations 58 of the face plate 20, and the knob 34 was then rotated until the hub stop pin 60 came into contact with the open stop 62. In this open position of the clamp-adjusting knob 34 the elastic cord 38 is rolled up on the hub 36 thereby moving the elastic cord 38 to, in turn, move the upper movable-jaw follower 26b and the attached movable jaw 14 upwardly and outwardly.

Now assuming that hospital personnel must quickly place a patient who is attached to an IV-tubing system on the mobile patient support 26 and transport the patient a long distance. When the patient is placed on the mobile patient support 68, his IV-pole 74, which is on castors (not shown), is rolled between the movable-jaw mouth 22 and the fixed-jaw mouth 24. The clamp-adjusting knob 34 is then depressed and rotated to the closed position in which gravity causes the first movable jaw 14 to move downwardly and to the right as viewed in FIG. 1 so that the movable-jaw and fixed-jaw mouths 22 and 24 move together on the IV-pole 74, thereby clamping it between them. In this regard, as the operator rotates the clamp-adjusting knob 34 to the closed position the elastic cord 38 is unrolled from the hub 36 thereby allowing slack in the elastic cord between hub 36 and the upper movable jaw follower 26b so that gravity could cause the movable jaw to move downwardly. The operator then lifts and releases the IV-pole and its weight causes further downward pressure on the movable jaw 14 via the resilient layer 32 on the movable-jaw mouth 22 which forces significant further engagement of the movable jaw 14 with the IV-pole 74, since the movable-jaw 14 is now operating at high mechanical advantage portions of the lower and upper slots 28a and b. It should be noted that all of these procedures can be performed by the operator with one hand thus leaving his other hand free for doing other things.

Now the patient is transported on the mobile patient support 68 to a new location, the IV-pole and its heavy contents being securely attached thereto and carried therewith, off the ground. At this new location assume that the patient must be moved to another support, such as a bed or wheelchair, where the IV-pole 74 will be disconnected from the mobile patient support 68 to stay with the patient supported on its own casters. Before removing the IV-pole 74 from the mobile patient support 68, the clamp-adjusting knob 34 is depressed and rotated so that it is in the open position and then released. The knob-position bias spring 42 forces engagement of the protrusions and indentations 56 and 58 at this open location and thereby ensures that the clamp-adjusting knob 34 and the hub 36 remain at this location. However, since the movable jaw 14 is tightly clamped onto the IV-pole 74, and is held clamped thereto by the weight of the IV-pole, it and its upper movable-jaw follower 26b do not move. This means that the elastic cord 38 must, and does, stretch to allow the movable jaw 14 to remain in the closed position even though the clamp-adjusting knob 34 has been moved to the open position. The operator can, then, with one hand, which is the same hand with which he rotated the clamp-adjusting knob 34, lift the IV-pole from the clamp and, immediately upon doing so, movable jaw 14 snaps to the open position under biasing force of the elastic cord 38. The operator can then lower the IV-pole to the ground.

It will be understood by those of ordinary skill in the art that the pole clamp assembly of this invention is extremely easy for an operator to use, since he can mount and dismount a heavy IV-pole to and from the clamp assembly with only one hand, thereby leaving his other hand free. Further, the pole clamp assembly of this invention is quite sturdy, so that it will hold extremely heavy life-support poles, including IV-poles. Since the mouths 22 and 24 of the jaws 14 and 16 are concaved slots which enclose the pole 74, they hold the pole sturdily, preventing it from falling laterally outwardly as well as in any other direction. Under normal circumstances, this would make it difficult to place the pole between the jaws and remove it therefrom, but the selective-actuatable biasing mechanism of this invention allows an operator to accomplish this with one hand.

While the invention has been particular shown and described with reference to a preferred embodiment, it will be understood by those skilled in the art that various changes in form in detail may be made therein without departing from the spirit and scope of the invention. For example, the housing 12 could be shaped quite differently than the housing depicted herein. Further, rather than using protrusions and indentations to maintain positions of the clamp-adjusting knob 34, other mechanisms could be used. In this regard, it is possible to include a mechanism for automatically moving the hub 36 to the closed position in response to the IV-pole being placed between the movable and fixed jaws; in fact, a further embodiment for doing this is described below.

In the preferred embodiment, shock cord is used as the elastic cord 38, however, other elastic cords could also be used. The housing could be bolted directly to a bed or other patient support or it could be clamped thereto by adapters or hooked thereon.

In a preferred embodiment, the resilient layers 32 are of a closed cell foam rubber so that they are soft and compressible, thereby allowing them to squeeze the IV-pole 74 as well as to tightly grip it and thereby be substantially influenced by its weight.

The knob 34 and its shaft and hub could be mounted directly on the housing, without the shaft passing through the fixed jaw 16.

It would also be possible for the elastic cord 38 to be in the form of an endless member which extends about the hub 36 having both ends attached to the movable-jaw followers. In this case, when the clamp-adjusting knob 34 is moved to a closed position, the elastic cord positively moves the movable jaw 14 as well as it being acted on by gravity as described above. In the same manner, the clamp-adjusting knob can be used to bias the movable jaw toward a closed position if it is being held in an open position.

Figure 4:
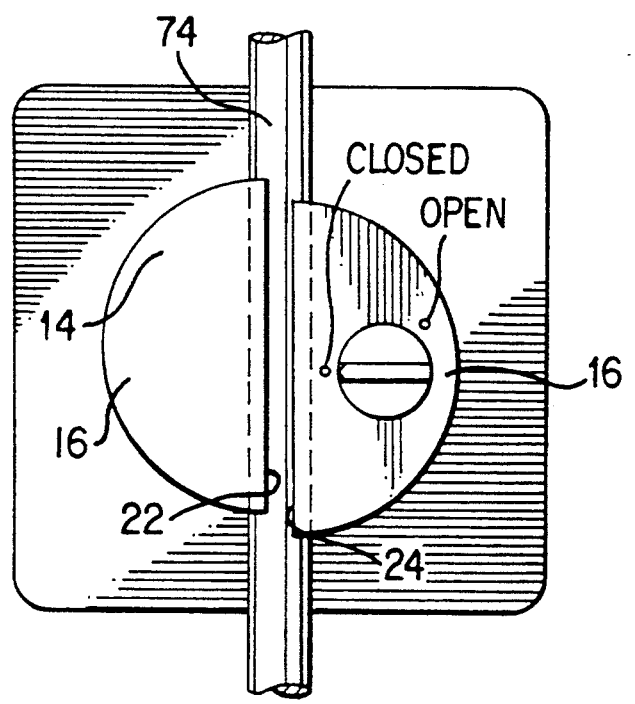
FIG. 4 is a front elevational view of the pole clamp assembly of FIG. 1 with a life-support, or IV pole clamped therein being depicted in fragmented fashion.
Figure 5:
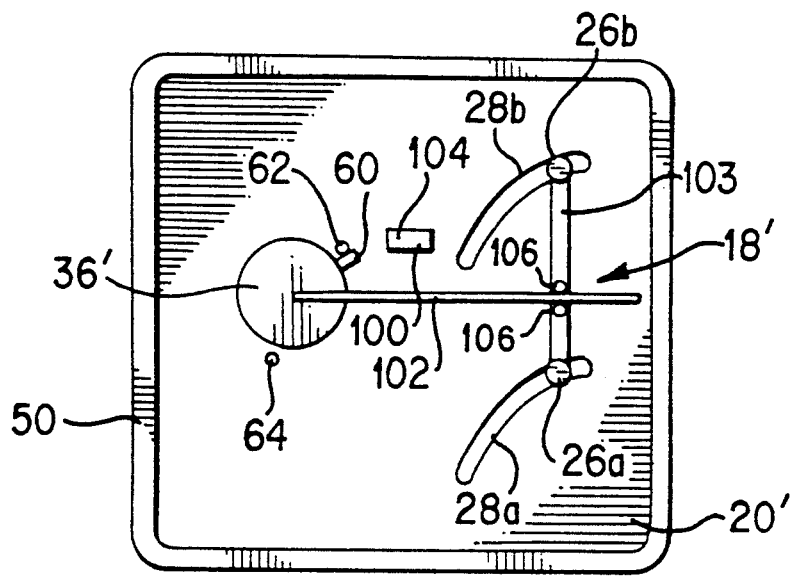
FIG. 5 is a rear elevational view, with a back plate totally removed, of another embodiment of this invention.
Figure 6:
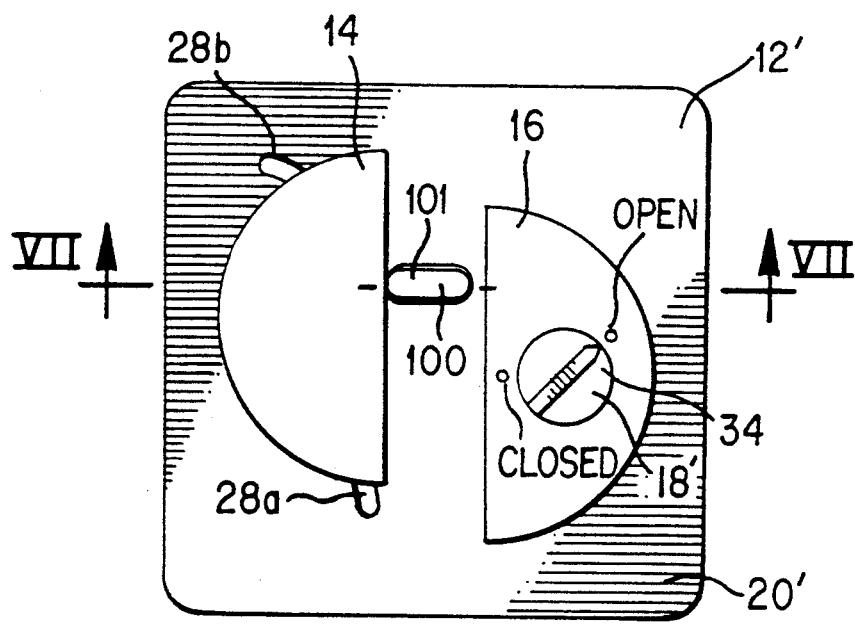
FIG. 6 is a front elevational view of the embodiment of FIG. 5.
Figure 7:
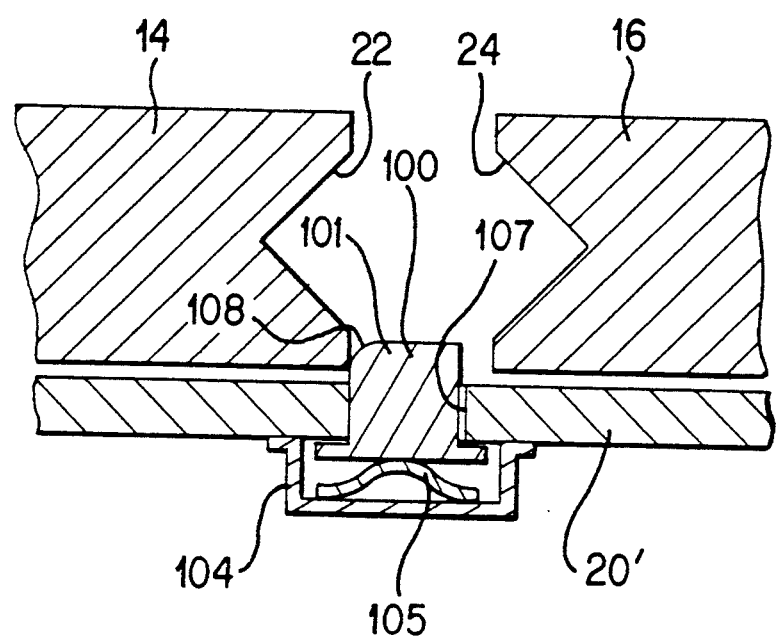
FIG. 7 is an enlarged segmental cross-sectional view taken along lines VII—VII of FIG. 6.

In fact, another preferred embodiment of this invention is depicted in FIGS. 5-7. This embodiment differs from the embodiment of FIGS. 2-4 in two ways. Firstly, the selectively actuatable biasing mechanism 18' is an elongated leaf spring lever 102 and this embodiment includes a jaw lock 100. Looking first at the selectively-actuatable biasing mechanism 18', the leaf spring lever 102 is affixed to the hub 36' to be rotatable therewith and slidable engages at an outer end thereof guides 106 which are affixed to a spacer bar 103 which is pivotally attached to the lower and upper movable-jaw followers 26a and b. Thus, when the hub 36' is rotated by rotating the clamp adjusting knob 34, as is described above for the embodiments FIGS. 1-4, the spring lever 102 impinges on the guides 106 to move the movable-jaw followers 26a and b between open and closed positions in which the first and second jaws 14, 16 are respectively far apart and close together. That is, when the hub stop pin 60 impinges on the open stop 62, the spring lever 102 is in a position for positioning the first movable jaw 14 to the open position. Similarly, when the hub stop pin 60 impinges on the closed stop 64 the spring lever 102 is in a position for placing the movable jaw 14 in the closed position. If, for example, the movable jaw 14 is held in the open position when the hub 36 is moved to a closed position, the spring lever 102 will flex and bow, thereby allowing the movable jaw 14 to stay in the open position when the hub is moved to the closed position, but creating a bias on the movable jaw 14 toward the closed position. The spring lever 102 can be formed of piano wire.

Another possible alternative to this structure is to make the lever 102 rigid and have it attached to the spacer bar 103 by means of a spring, or an elastic member. Also, the lever 102 could be attached to the movable-jaw followers 26a and b without using a keeper, or spacer, bar 103.

The jaw lock 100 comprises a latch 101, a bracket 104, and a spring 105. The face plate 20' has a lock opening 107 therein through which the latch 101 extends. The bracket 104 is affixed to the rear surface of the face plate 20' to hold the spring 105 pressing against the latch 101 to cause the latch 101 to extend outwardly and thereby engage the mouth 22 of the movable jaw 14 and hold it in an open configuration. When something is inserted between the mouths 22 and 24 of the movable-jaw 14 and the fixed jaw 16, such as an IV-pole, it impinges on an outer end of the latch 101 thereby driving the latch 101 back through the lock opening 107 of the face plate 20', against a force of the spring 105. Eventually, a rounded edge 108 of the latch 101 clears the mouth 22 and allows the movable jaw 14 to move to a closed position.

Operation of the FIG. 5-7 device is quite similar to that of the FIGS. 1-4 device in that the movable jaw 14 is moved to the open position as depicted in FIG. 6 by rotating the hub 36', via the knob 34, to the open position with the hub stop pin 60 impinging on the open stop 62. The movable jaw 14 is then held cocked in this position by the latch 101 as depicted in FIG. 7. When an operator is ready to mount an IV-pole on the clamp, he moves the hub 36' to a closed position with the hub stop pin 60 impinging on the closed stop 64 which bows the spring lever 102, thereby placing a bias on the movable jaw 14 toward the closed position. However, the movable jaw 14 cannot move to this position because it is being held in the open position by the latch 101. When the operator inserts an IV-pole between the mouths 22 and 24 the IV-pole pushes the latch 101 back through the face plate 20' so that the latch 101 clears the movable jaw 14 and allows it to snap to a closed position. The operator then lifts the IV-pole off the ground and allows its weight to further close the jaws. When the operator is ready to remove the IV-pole, he rotates the hub 36' by rotating the knob 34, until the hub stop pin 60 impinges on the open stop 62 and lifts the IV-pole from between the mouths 22 and 24. The spring lever 102, which is now placing a bias on the movable jaw 14, snaps the movable jaw 14 to the open position, thereby allowing the operator to move the IV-pole from between the clamp.

The spring 105 is depicted as a leaf spring, but could also be a coil spring.

It will be appreciated by those of ordinary skill in the art that the FIGS. 5-7 embodiment can function right-side-up or upside-down, unlike the FIGS. 1-4 embodiment, which requires the use of gravity.

It will, of course, be recognized by those skilled in the art that the latch 101 could be configured quite differently than that shown in FIGS. 5-6 and still be within the scope of this invention.

It should also be understood to those of ordinary skill in the art that the lower and upper slots 28a and b could be replaced by equal length levers which are pivotally attached to the movable jaw and the face plate 20 at equally spaced pivot points. There are other equivalent linkages which could be used to replace the slots 28a and b of this invention.

It is also possible for both jaws to be movable rather than only one.

Further, the pole clamp of the embodiment of FIGS. 1-4 of this invention can be turned upside-down, attached to a pump or other equipment, and then used to attach the equipment to a pole in the same manner as described above.

Also, it is possible for the clamp of this invention to be arranged so that the selectively-actuatable biasing mechanism is placed in a closed position but with the movable jaw in an open position and biased toward the closed position. This is the case when each end of the elastic cord is attached to the movable jaw and when the spring lever is used as are described above.

The hub, pulley, or reel 36 could be replaced with levers or other mechanical devices.

Although the clamp assembly of this invention is described in a medical setting, it would also be possible to use it in other settings, such as sailing and the like. The invention can be used anywhere where equipment must be mounted to vertical poles or poles need to be securely mounted to other structures.

The embodiments of the invention in which an exclusive property or privilege are claimed are defined as follows:

1. A pole clamp assembly comprising:
   a base frame;

two jaws mounted on said base frame, said base frame and said jaws including a movement-allowing means for allowing at least the first of said jaws to be movable between a closed position in which it is relatively close to the second jaw and an open position in which it is spaced further from the second jaw;

a selectively actuatable biasing means linked to said movable jaw for being selectively switched between a biasing mode in which it allows said movable jaw to be held in one of said closed and open positions, while urging said movable, first, jaw towards said other position and a non-biasing mode in which it allows said movable jaw to be in said one of the closed and open positions without substantially urging said movable jaw towards said other position.

2. A pole clamp assembly as in claim 1 wherein said movement-allowing means increases mechanical advantage of force of said movable jaw as said jaw approaches said closed position, whereby a constant force applied to said movable jaw to move said jaw towards said second jaw causes said clamp assembly to grip a pole between said movable and said second jaws with an increasingly greater force.

3. A pole clamp assembly as in claim 2 wherein said movement-allowing means comprises a curved track on a base frame which curves from a direction perpendicular to an interface between the two jaws at a location furthest from the interface toward a direction parallel to the interface at a location closest to the interface, whereby said movable and second jaws can be clamped tightly on said pole placed therebetween by the application of a relatively little force.

4. A pole clamp assembly as in claim 3 wherein there are two curved tracks.

5. A pole clamp assembly as in claim 3 wherein said track is formed by a slot in the base frame.

6. A pole clamp assembly as in claim 5 wherein said selectively-actuatable biasing means comprises an elastic cord attached to the movable jaw and a selectively movable mechanism for engaging the elastic cord and being selectively moved between a closed and an open position to thereby selectively move the movable jaw between said closed and open positions.

7. A pole clamp assembly as in claim 6 wherein said selective-actuatable biasing means includes a fixing means for fixing said selectively movable mechanism in either said closed or said open position thereof.

8. A pole clamp assembly as in claim 7 wherein said selective-actuatable biasing means includes a hub around which said elastic cord coil is turned and said fixing means engages said hub in either of two angular positions corresponding to said open and closed positions thereof.

9. A pole clamp assembly as in claim 1 wherein said selectively-actuatable biasing means comprises an elastic cord attached to the movable jaw and a selectively movable mechanism for engaging the elastic cord which is for being selectively moved between a closed and an open position to thereby selectively change an elastic bias acting on the movable jaw by said elastic cord along a path between said closed and open positions.

10. A pole clamp assembly as in claim 9 wherein said selective-actuatable biasing means includes a fixing means for fixing said selectively movable mechanism in either said closed or said open position thereof.

11. A pole clamp assembly as in claim 10 wherein said selective-actuatable biasing means includes a hub around which said elastic cord coil is turned and said fixing means engages said hub in either of two angular positions corresponding to said open and closed positions thereof.

12. A pole clamp assembly as in claim 1 wherein said pole clamp assembly further includes a mobile patient support and is clamped onto an IV-pole for holding life-support equipment for patients supported by said mobile patient support.

13. A pole clamp assembly as in claim 1 wherein said pole clamp assembly further comprises a locking means for locking said first jaw in said open position and for impinging on an object placed between said jaws to release said first jaw in response thereto.

14. A pole clamp assembly as in claim 1 wherein said selectively actuatable biasing means comprises an elongated lever.

15. A method of clamping a life-support pole, such as an IV-pole, to a mobile patient support comprising the steps of:
mounting a base frame on the mobile patient support;
mounting at least two jaws on the base frame with at least a first, movable jaw thereof being mounted for movement on the base frame to be movable between a closed position, in which it is relatively close to the second jaw, and an open position, in which it is further removed from the second jaw;
mounting a selectively actuatable biasing means between the base frame and the movable jaw which can be selectively switched between a biasing mode in which it allows the movable jaw to be held in said closed position while urging said movable jaw toward said open position and a non-biasing mode in which it allows said movable jaw to be in the closed position without substantially urging said movable jaw toward said open position;
placing said selectively actuatable biasing means in said biasing mode;
placing said pole between said jaws;
placing said selectively actuatable biasing means in said non-biasing mode.

16. A method as in claim 15 wherein is further included the step of unclamping said pole from said mobile patient support comprising the sub-steps of placing said selectively actuatable biasing means in said biasing mode while said pole is clamped between said first and second jaws;
lifting said life-support pole from said jaws, thereby allowing said first movable jaw to snap to an open position under the urging of said selectively actuatable biasing means.

17. A method as in claim 15 wherein said step of placing said pole between said jaws includes the sub-step of lifting said pole off the ground.

18. A method as in claim 15 wherein said step of placing said selectively actuatable biasing means in said biasing mode is carried out before said step of placing said pole between said jaws.

* * * * *